United States Patent [19]

White et al.

[11] Patent Number: 5,464,433

[45] Date of Patent: Nov. 7, 1995

[54] ATRIAL DEFIBRILLATOR AND METHOD PROVIDING DUAL RESET OF AN INTERVAL TIMER

[75] Inventors: Harley White, Redmond; John M. Adams, Issaquah, both of Wash.

[73] Assignee: InControl, Inc., Redmond, Wash.

[21] Appl. No.: 259,515

[22] Filed: Jun. 14, 1994

[51] Int. Cl.⁶ .................................................. A61N 1/39
[52] U.S. Cl. ................................................................ 607/5
[58] Field of Search ........................... 607/5, 4; 128/706

[56] References Cited

U.S. PATENT DOCUMENTS

| | | | |
|---|---|---|---|
| 5,207,219 | 5/1993 | Adams et al. | 607/5 |
| 5,275,621 | 1/1994 | Mehra | 607/5 |
| 5,282,837 | 2/1994 | Adams | 607/5 |
| 5,411,524 | 5/1995 | Rahul | 607/5 |

Primary Examiner—William E. Kamm
Assistant Examiner—Kennedy J. Schaetzle
Attorney, Agent, or Firm—Richard O. Gray, Jr.

[57] ABSTRACT

An implantable atrial defibrillator for applying cardioverting electrical energy to the atria of a human heart. The atrial defibrillator includes a first detector for sensing a depolarization activation wave at a first pair of locations of the heart and generating a first initiation signal and a second detector for sensing the depolarization activation wave between a second pair of locations of the heart and generating a second initiation signal. The atrial defibrillator also includes a timing circuit for timing the time between immediately successive depolarization activation waves of the heart in response to one of the first and the second initiation signals for commencing the timing. The atrial defibrillator also includes a cardioverting circuit for applying the cardioverting electrical energy to the atria of the heart when the atria of the heart are in need of cardioversion and when the timer times a time greater than a predetermined time interval.

16 Claims, 7 Drawing Sheets

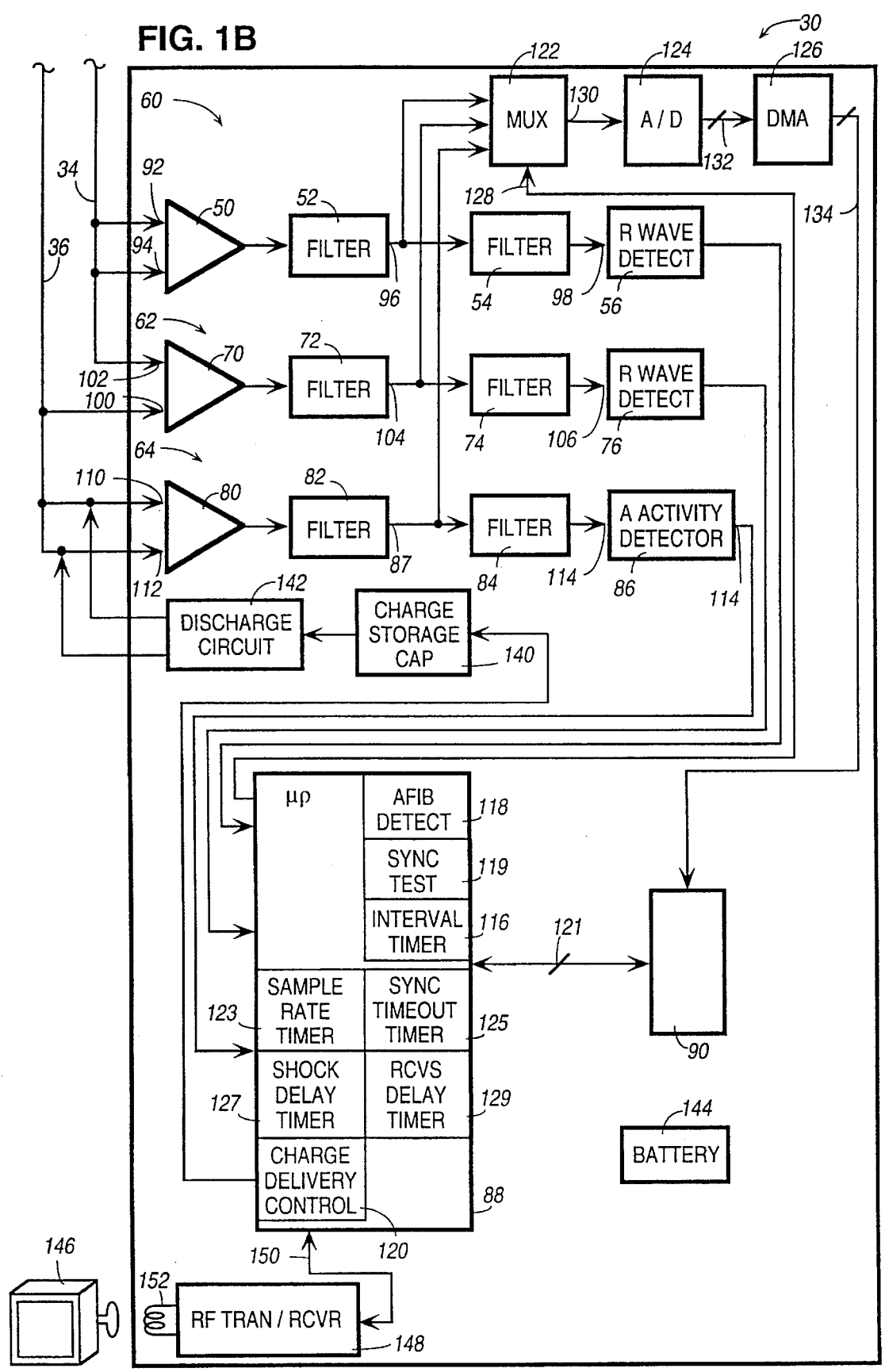

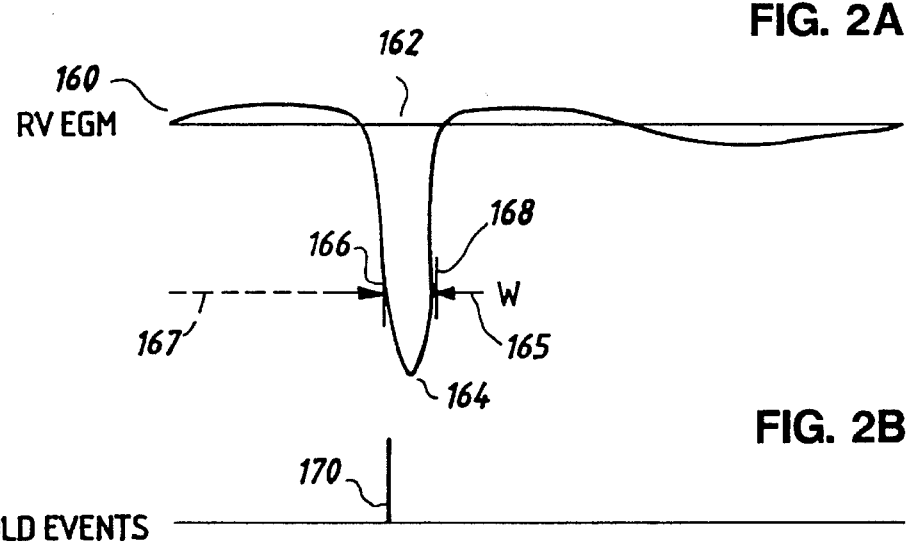
FIG. 2A
FIG. 2B
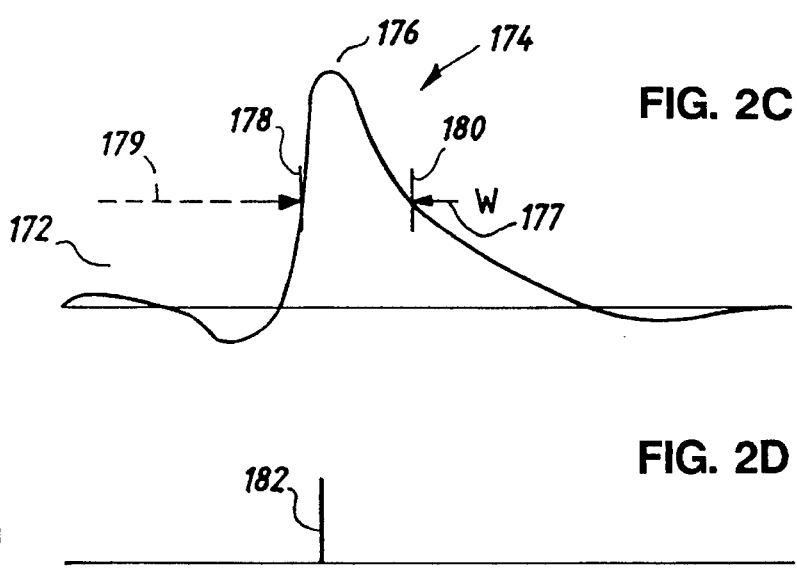
FIG. 2C
FIG. 2D

ATRIAL DEFIBRILLATOR AND METHOD PROVIDING DUAL RESET OF AN INTERVAL TIMER

BACKGROUND OF THE INVENTION

The present invention generally relates to an atrial defibrillator for applying cardioverting electrical energy to the atria of a human heart in need of cardioversion. The present invention is more particularly directed to a fully automatic implantable atrial defibrillator which exhibits improved safety by reducing the potential risk of induced ventricular fibrillation which may result from the mistimed delivery of cardioverting electrical energy to the atria of the heart. More specifically, the atrial defibrillator of the present invention guards against applying cardioverting electrical energy to the atria of the heart under conditions believed to contribute to induced ventricular fibrillation.

Atrial fibrillation is probably the most common cardiac arrhythmia. Although it is not usually a life-threatening arrhythmia, it is associated with strokes thought to be caused by blood clots forming in areas of stagnant blood flow as a result of prolonged atrial fibrillation. In addition, patients afflicted with atrial fibrillation generally experience palpitations of the heart and may even experience dizziness or even loss of consciousness.

Atrial fibrillation occurs suddenly and many times can only be corrected by a discharge of electrical energy to the heart through the skin of the patient by way of an external defibrillator of the type well known in the art. This treatment is commonly referred to as synchronized cardioversion and, as its name implies, involves applying cardioverting or defibrillating electrical energy to the heart in synchronism with a detected depolarization activation wave (R wave) of the heart. The treatment is very painful and, unfortunately, most often only results in temporary relief for patients, lasting but a few weeks.

Drugs are available for reducing the incidence of atrial fibrillation. However, these drugs have many side effects and many patients are resistant to them which greatly reduces their therapeutic effect.

Implantable atrial defibrillators have been proposed to provide relief to patients suffering from occurrences of atrial fibrillation. Unfortunately, to the detriment of such patients, none of these atrial defibrillators have become a commercial reality.

Implantable atrial defibrillators proposed in the past have exhibited a number of disadvantages which probably have been the cause of these defibrillators failing to become a commercial reality. Two such proposed defibrillators, although represented as being implantable, were not fully automatic, requiring human interaction for cardioverting or defibrillating the heart. Both of these defibrillators require the patient to recognize the symptoms of atrial fibrillation with one defibrillator requiring a visit to a physician to activate the defibrillator and the other defibrillator requiring the patient to activate the defibrillator from external to the patient's skin with a magnet.

Improved atrial defibrillators and lead systems which exhibit both automatic operation and improved safety are fully described in U.S. Pat. No. 5,282,837, issued Feb. 1, 1994 in the names of John M. Adams and Clifton A. Alferness for "Improved Atrial Defibrillator and Method" and U.S. application Ser. No. 07/856,514, filed Mar. 24, 1992 in the in the names of John M. Adams, Clifton A. Alferness, and Paul E. Kreyenhagen for "Improved Atrial Defibrillator, Lead Systems, and Method", now U.S. Pat No. 5,433,729, which patents are assigned to the assignee of the present invention and incorporated herein by reference. As disclosed in the aforementioned referenced patents, synchronizing the delivery of the defibrillating or cardioverting electrical energy to the atria with a ventricular electrical activation (R wave) of the heart is important to prevent induced ventricular fibrillation. Ventricular fibrillation is a fatal arrhythmia which can be caused by electrical energy being delivered to the heart at the wrong time in the cardiac cycle, such as during the T wave of the cycle. The atrial defibrillators of the aforementioned referenced applications exhibit improved safety from inducing ventricular fibrillation by sensing ventricular activations of the heart in a manner which avoids detecting noise as ventricular electrical activations for generating reliable synchronization signals. Hence, these implantable atrial defibrillators, by providing such noise immunity in R wave detection, assure reliable synchronization.

The aforementioned U.S. Pat. No. 5,282,837 describes non-coincident sensing of an electrical activation such as an R wave at two different areas of the heart to provide a reliable indication that the sensed electrical activation is a real or legitimate electrical activation and not noise or other interference. Non-coincidentally sensed electrical activations, in accordance with the teachings of U.S. Pat. No. 5,282,837, are considered to be legitimate electrical activations. Others are considered to be noise or other interference. The non-coincidentally sensed electrical activation thus can be relied upon for synchronizing the delivery of a defibrillating or cardioverting electrical pulse to the atria.

It has further been observed that during episodes of atrial fibrillation, the cardiac rate increases to a high rate and/or becomes extremely variable. At high cardiac rates, the R wave of each cardiac cycle becomes closely spaced to the T wave of the immediately preceding cardiac cycle. This may lead to a condition known in the art as an "R on T" condition, which is believed to contribute to induced ventricular fibrillation if the atria are cardioverted in synchronism with an R wave close to a T wave.

An atrial defibrillator and method which greatly reduces the risk of inducing ventricular fibrillation during atrial cardioversion or defibrillation by avoiding applying the cardioverting electrical energy to the atria at those instances when increased vulnerability to ventricular fibrillation may be present is described in U.S. Pat. No. 5,207,219, issued May 4, 1993 to John M. Adams, Clifton A. Alferness, Kenneth R. Infinger, and Joseph M. Bocek, which patent is assigned to the assignee of the present invention and incorporated herein by reference. As described in the referenced patent, this is accomplished by interval timing prior to applying the cardioverting or defibrillating electrical energy. The time interval between immediately successive R waves is timed by an interval timer and the cardioverting or defibrillating electrical energy is only applied when the interval timer times an interval which is greater than a preselected minimum interval. This provides protection from the increased vulnerability to ventricular fibrillation resulting from a high cardiac rate.

U.S. Pat. No. 5,207,219 contemplates, in accordance with a preferred embodiment, the resetting of the interval timer responsive to R waves detected in the right ventricle of the heart. However, while this is generally successful, it has been learned that R waves detected in the right ventricle during atrial fibrillation have highly variable amplitudes. Hence, as an added measure of safety, it would be desirable to sense or detect R waves at more than one location of the heart and reset the interval timer responsive to an R wave detected at any one of the R wave detection locations. This will assure reliable timing initiation by the interval timer notwithstanding the variability of the amplitudes of depolarization activation waves sensed at any one location of the heart. Hence, while an R wave may be missed due to an extremely low amplitude at one location of the heart, it will still be detected at another location for resetting the interval timer.

The atrial defibrillator and method of the present invention greatly reduces the risk of inducing ventricular fibrillation during atrial cardioversion or defibrillation by avoiding applying cardioverting electrical energy to the atria at those instances when increased vulnerability to ventricular fibrillation may be present. As will be seen hereinafter, this is accomplished by interval timing prior to applying the cardioverting or defibrillating electrical energy. The time interval between immediately successive R waves is timed and the cardioverting or defibrillating electrical energy is applied only when a timed interval is greater than a preselected minimum interval. Timing is reset in response to sensing a depolarization activation wave in one of a first area and a second area of the heart to assure that all R waves are used for resetting the interval timing.

SUMMARY OF THE INVENTION

The present invention therefore provides an implantable atrial defibrillator for applying cardioverting electrical energy to the atria of a human heart. The atrial defibrillator includes first detecting means for sensing a depolarization activation wave at a first location of the heart and generating a first initiation signal. The atrial defibrillator further includes second detecting means for sensing the depolarization activation wave at a second location of the heart and generating a second initiation signal. The atrial defibrillator still further includes timing means for timing the time between immediately successive depolarization activation waves of the heart in response to at least one of the first and the second initiation signals for commencing the timing. The atrial defibrillator still further includes cardioverting means for applying the cardioverting electrical energy to the atria of the heart when the atria of the heart are in need of cardioversion and when the timing means times a time greater than a predetermined time interval.

The present invention further provides a method of applying cardioverting electrical energy to the atria of a human heart in need of cardioversion. The method includes the steps of detecting a depolarization activation wave at a first location of the heart and generating a first initiation signal responsive thereto. The method further includes the steps of detecting the depolarization activation wave of the heart at a second location of the heart and generating a second initiation signal responsive thereto. The method includes the further steps of timing the time between successive depolarization activation waves of the heart and commencing the timing in response to at least one of the first and the second initiation signals. The invention still further includes the step of applying the cardioverting electrical energy to the atria of the heart when the atria of the heart are in need of cardioversion and when the time between immediately successive depolarization activation waves is greater than a predetermined time interval.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like reference numerals identify identical elements, and wherein:

FIG. 2 is a series of wave forms representative of electrical activity of a human heart detected by the atrial defibrillator of FIG. 1;

DETAILED DESCRIPTION OF THE PREFERRED EMBODIMENT

Figure 1A:
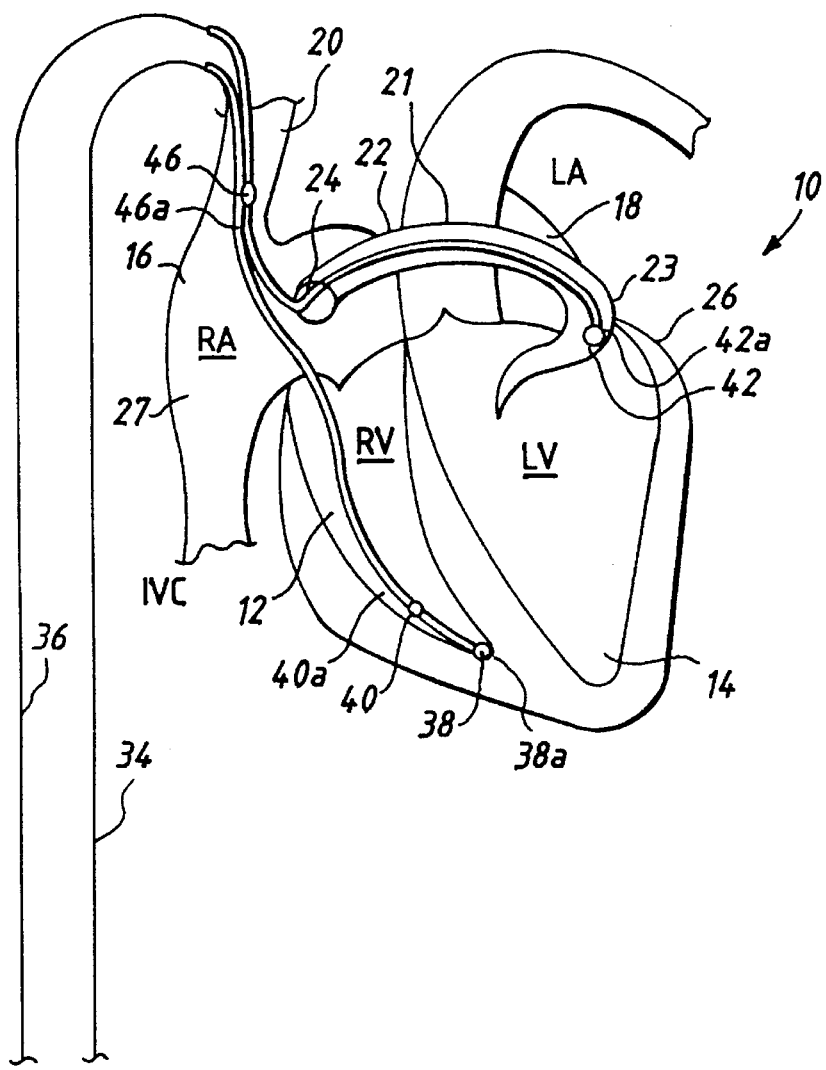
FIG. 1 is a schematic block diagram of a fully implantable atrial defibrillator embodying the present invention in accordance with the preferred embodiment thereof and shown in association with a human heart in need of atrial fibrillation monitoring and potential cardioversion of the atria.
Figure 1:
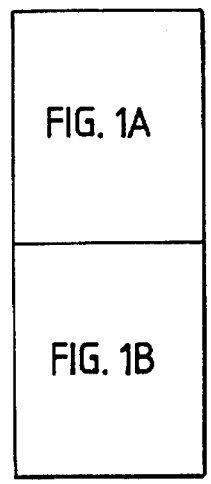

Referring now to FIG. 1, it illustrates a fully implantable atrial defibrillator 30 embodying the present invention shown in association with a schematically illustrated human heart 10 in need of atrial fibrillation monitoring and potential cardioversion of the atria. The portions of the heart illustrated in FIG. 1 are the right ventricle 12, the left ventricle 14, the right atrium 16, the left atrium 18, the superior vena cava 20, the coronary sinus channel 21 which, as used herein, denotes the coronary sinus 22 and the great cardiac vein 23, the coronary sinus ostium or opening 24, the left ventricular free wall 26 and the inferior vena cava 27. In addition, as used herein, the term "depolarization activation waves" denotes R waves of the heart cardiac cycle which induce depolarizations of the ventricles 12 and 14.

The atrial defibrillator 30 generally includes an enclosure 32 for hermetically sealing the internal circuit elements of the atrial defibrillator 30, an endocardial first lead 34 and an intravascular second lead 36. The second lead 36 may alternatively comprise two leads. A single lead is illustrated in FIG. 1 so as to not unduly complicate the figure. The enclosure 32 and the first and second leads 34 and 36 are arranged to be implanted beneath the skin of a patient so as to render the atrial defibrillator 30 fully implantable.

The endocardial first lead 34 preferably comprises an endocardial bipolar lead having electrodes 38 and 40 arranged for establishing electrical contact with the right ventricle 12 of the heart 10. The electrodes 38 and 40 permit bipolar sensing of depolarization activation waves in the right ventricle between a first pair of locations 38a and 42a within the right ventricle 12. As illustrated, the lead 34 is fed through the superior vena cava 20, into the right atrium 16, and then into the right ventricle 12. As will be appreciated by those having ordinary skill in the art, a second path for lead 34 could alternatively be through the inferior vena cava 28, into the right atrium 16, and then into the right ventricle 12.

The second lead 36 generally includes a first or distal electrode 42 and a second electrode 46. As illustrated, the second lead 36 is flexible and arranged to be passed down the superior vena cava 20, into the right atrium 16, into the coronary sinus ostium 24, and advanced into the coronary sinus channel 21 of the heart near the left side thereof. The first or distal electrode 42 is preferably within the coronary sinus 22 or the great vein 23 of the heart adjacent to the left ventricle 14 at a location 42a. The electrode 42 is preferably elongated such that the electrode 42 is within the coronary sinus 22 and/or the great cardiac vein 23 adjacent the left ventricle 14 and beneath the left atrium 18. The second electrode 46 is preferably located at a location 46a within either the right atrium 16 or the superior vena cava 20 and preferably within the right atrium 16.

As indicated above, the second lead 36 may comprise two leads. In this preferred embodiment, one of the two leads may include the first electrode 42 and the other of the two leads may include the second electrode 46. As noted above, the first electrode 42 and the second electrode 46 are illustrated in FIG. 1 as combined on a single lead, the second lead 36, so as not to unduly complicate the figure.

The first electrode 42 together with the second electrode 46 of the second lead 36 provide for the delivery of defibrillating or cardioverting electrical energy to the atria. Because the first electrode 42 is located beneath the left atrium 18 near the left ventricle 14 and the second electrode 46 is within either the right atrium 16 or the superior vena cava 20 and above the coronary sinus ostium 24, the electrical energy applied between these electrodes will be substantially confined to the atria 16 and 18 of the heart 10. As a result, the electrical energy applied to the right ventricle 12 and left ventricle 14 when the atria are cardioverted or defibrillated will be minimized.

Within the enclosure 32, the atrial defibrillator 30 includes a first or right ventricular (RV) channel 60, a second or right ventricular-coronary sinus (RVCS) channel 62 and a third or atrial channel 64. The RV channel 60 includes a first sense amplifier 50, a first filter 52, a second filter 54 and an R wave detector 56. The RVCS channel 62 includes a second sense amplifier 70, a third filter 72, a fourth filter 74 and a second R wave detector 76. The atrial channel 64 includes a third sense amplifier 80, a fifth filter 82, a sixth filter 84 and an atrial activity detector 86. Within the enclosure 32, the atrial defibrillator 30 also includes a microprocessor 88 and a memory 90.

The first sense amplifier 50 includes a first input 92 which is coupled to electrode 38 of the first lead 34 and a second input 94 which is coupled to electrode 40 of the first lead 34. The first sense amplifier 50 amplifies the sensed electrical activity of the heart. The first filter 52 conditions the sensed electrical activity of the heart and provides at an output 96 an amplified input signal representative of the electrical activity of the heart such as depolarization activation waves sensed by the bipolar electrodes 38 and 40 in the right ventricle 12 of the heart 10. The first sense amplifier 50 may include one or more gain stages, and the order of the first sense amplifier 50 and the first filter 52 may be reversed. That is, the first filter 52 may be coupled between the electrodes 38 and the first sense amplifier 50. The second filter 54 further conditions the sensed electrical activity of the heart.

The first R wave detector 56 has an input 98 coupled to the second filter 54. The first R wave detector 56 produces an electrical output or an initiation signal corresponding to the depolarization activation wave sensed by the first sense amplifier 50 when the amplified input signal received at the input 98 of the first R wave detector 56 exceeds a threshold.

As a result, the RV channel 60, including electrodes 38, 40, the sense amplifier 50, the first filter 52, the second filter 54 and the R wave detector 56, forms a first detecting means for sensing a depolarization activation wave in general at a first location of the heart, and more specifically, between a first pair of locations 38a and 42a of the heart for generating a first initiation signal. The electrodes 38 and 40 and the first sense amplifier 50 form a first sensing means for sensing the depolarization activation wave. The first R wave detector 56 forms a first output means for generating the first initiation signal in response to the first sensing means.

The RVCS channel 62 preferably operates in a manner similar to the operation of the RV channel 60. The second sense amplifier 70 includes a first input 100 which is coupled to the electrode 42 of the second lead 36 and a second input 102 which is coupled to electrode 38 of the first lead 34. The second sense amplifier 70 amplifies the sensed electrical activity of the heart. The third filter 72 conditions the sensed electrical activity and provides at an output 104 an amplified signal representative of the electrical activity of the heart, such as depolarization activation waves sensed by electrodes 38 and 42. The second sense amplifier 70 may include one or more gain stages. The fourth filter 74 further conditions the amplified electrical activity.

The second R wave detector 76 includes an input 106 for receiving the amplified signal. The second R wave detector 76 produces an electrical output or an initiation signal when the amplified input signal provided at the input 106 exceeds a threshold.

As a result, the RVCS channel, including the electrode 42, the electrode 38, the second sense amplifier 70, the third filter 72, the fourth filter 74 and the R wave detector 76, form a second detecting means for sensing a depolarization activation wave in general at a second location of the heart, and more specifically, between a second pair of locations 38a and 42a of the heart for generating a second initiation signal. The second sense amplifier 70 and the third filter 72 form a second sensing means for sensing the depolarization activation wave. The R wave detector 76 forms a second output means for generating the second initiation signal in response to the second sensing means.

The third sense amplifier 80 senses electrical activity in the atria 16 and 18 of the heart 10. To that end, the third sense amplifier 80 includes a first input 110 which is coupled to electrode 46 and a second input 112 which is coupled to electrode 42. The fifth filter 82 and the sixth filter 84 condition the amplified electrical activity sensed by the third sense amplifier 80. The atrial activity detector 86 includes an input 114 for receiving the conditioned, amplified electrical activity and an output 114 for providing an indication of electrical activity of the heart sensed by the third sense amplifier 80. As a result, the atrial channel 64, including the electrodes 42 and 46, the third sense amplifier 80, the fifth filter 82, the sixth filter 84 and the atrial activity detector 86, form a third detecting means for sensing activity of the atria of the heart.

The microprocessor 88 is preferably implemented in a manner as disclosed in the aforementioned U.S. Pat. No. 5,282,837 and further as described hereinafter with respect to the flow diagram of FIGS. 4 and 5. The implementation of the microprocessor 88 in accordance with this embodiment of the present invention results in a plurality of functional stages. The stages include an interval timer 116, an atrial arrhythmia detector in the form of an atrial fibrillation detector 118 and a charge delivery and energy control stage 120. The functional stages implemented by the microprocessor 88 also include a synchronization test 119, a sample rate timer 123, a synchronization timeout timer 125, a shock delay timer 127 and an RVCS delay timer 129, which will be discussed further in conjunction with FIGS. 4 and 5. The microprocessor 88 is arranged to operate in conjunction with the memory 90 which is coupled to the microprocessor 88 by a multiple bit address and data bus 121.

The atrial defibrillator 30 further includes an analog multiplexer 122, an analog-to-digital converter 124 and a direct memory access (DMA) controller 126. The output 96 of the first filter 52, the output 104 of the third filter 72 and the output 87 of the fifth filter 82 are coupled to the analog multiplexer 122. In response to control signals received from the microprocessor 88 at a control input 128, the analog multiplexer 122 couples signals received from either the first filter 52, the third filter 72, the fifth filter 82, or a time sequential combination of these signals to the output 130 of the analog multiplexer 122. The output 130 is coupled to the analog-to-digital converter 124, which converts analog signals received from the output 130 to digital data. The digital data are conveyed over a multiple bit data bus 132 to the direct memory access controller 126. The direct memory access controller 126 conveys digital data, along with storage address information, over a multiple bit bus 134 to the memory 90. As a result, data received from either the first filter 52, the third filter 72 or the fifth filter 82 are stored by the DMA controller 126 in the memory 90, without further intervention by the microprocessor 88.

For determining if the heart 10 is in need of cardioversion or defibrillation, and to synchronize delivery of cardioverting or defibrillating electrical energy with detection of a ventricular activation, the atrial defibrillator 30 acquires a multi-channel intracardiac electrogram (EGM) segment. To acquire a multi-channel EGM segment, the microprocessor 88 conveys control signals to the control input 128 of the analog multiplexer 122 to cause the analog multiplexer 122 to couple a periodic time sequential combination of two or more of the filter outputs 96, 104, or 87 to the output 130 of the analog multiplexer 122. The analog-to-digital converter 124 converts sequential analog signals from each of the requested filter outputs 96, 104, or 87 to digital data. The DMA controller 126 receives the digital data in a time-multiplexed format and stores the data in the memory 90.

In this manner, the atrial defibrillator 30 may store data corresponding to electrical activity of the heart sensed by each of the first sense amplifier 50, the second sense amplifier 70 and the third sense amplifier 80. Following acquisition of an EGM segment by the atrial defibrillator 30, the data which form the EGM segment may be analyzed by the microprocessor 88.

The atrial defibrillator 30 further includes a charger and storage capacitor circuit 140 of the type well known in the art which charges a storage capacitor to a predetermined peak voltage level and a discharge circuit 142 for discharging the storage capacitor within the circuit 140 for a predetermined time to provide a controlled discharge output of electrical energy when required to the atria of the heart 10. To that end, the discharge circuit 142 is coupled to the first electrode 42 and the second electrode 46 of the second lead 36 for applying the cardioverting or defibrillating electrical energy to the atria. The atrial defibrillator 30 further includes a depletable power source 144, such as a lithium battery, for providing power to the electrical components of the atrial defibrillator 30.

When the atrial fibrillation detector 118 determines that the atria 16 and 18 are in fibrillation and thus in need of cardioversion, the charge delivery control 120 causes the charger and storage capacitor circuit 140 to charge the storage capacitor within the circuit 140. The charge delivery control 120 causes the discharge circuit 142 to discharge the capacitor of the circuit 140 for applying cardioverting electrical energy to the atria 16 and 18 in synchronism with an R wave detected by first sense amplifier 50 and first R wave detector 56 and second sense amplifier 70 and second R wave detector 76.

For entering operating parameters into the microprocessor 88, the atrial defibrillator 30 receives programmable operating parameters from an external controller 146 which is external to the skin of the patient. The external controller 146 is arranged to communicate with a receiver/transmitter 148 within enclosure 32 which is coupled to the microprocessor 88 over a bidirectional bus 150. The receiver/transmitter 148 may be of the type well known in the art for conveying various information which it obtains from the microprocessor 88 to the external controller 146 or for receiving programming parameters from the external controller 146 which the receiver/transmitter 148 then conveys to the microprocessor 88 for storage in internal memory or in the memory 90 within the enclosure 32.

The receiver/transmitter 148 includes a transmitting coil 152. Such communication circuits are well known in the art and may be utilized as noted above for receiving commands from external to the implantable enclosure 32 and for transmitting data to the external controller 146 from the implanted enclosure 32.

Referring now to FIG. 2, it shows a series of wave forms representative of electrical activity of the human heart 10 detected by the atrial defibrillator 30 of FIG. 1. The wave forms of FIG. 2 are plotted with voltage on the vertical axis and time on the horizontal axis.

FIG. 2 shows a right ventricular intracardial electrogram (RV EGM) segment 160 which has been detected by the first sense amplifier 50 between a first pair of locations 38*a* and 40*a*. The RV EGM 160 may be converted to digital data by the analog-to-digital converter 124 and stored in the memory 90 by direct memory access controller 126 for analysis by the microprocessor 88. The RV EGM segment 160 includes a representation of a detected depolarization activation wave or R wave 162 which has a peak 164. The RV EGM 160 further has an initial portion 166 with a negative slope and a final portion 168 with a positive slope. The RV EGM 160 has a peak width 165 measured at a predetermined voltage 167.

FIG. 2 further shows a representation of a detected threshold event 170, as detected by the first R wave detector 56. The second filter 54 receives the RV EGM 160 from the first filter 52 and, after further conditioning, provides the RV EGM to the first R wave detector 56. When the signal level of the RV EGM exceeds a predetermined threshold, the R wave detector 56 provides an electrical indication such as RV threshold event 170 to the microprocessor 88. The detected RV threshold event 170 may be stored in memory 90 as the time at which the first R wave detector 56 detected a threshold event in the right ventricle 12 of the heart 10. The microprocessor 88 uses the detected threshold event 170, for example, to compare the time at which the threshold event 170 is detected with the timing of the RV EGM 160, as will be discussed further in conjunction with the flow diagram of FIGS. 4 and 5.

FIG. 2 further shows a right ventricular-coronary sinus intracardial electrogram (RVCS EGM) segment 172 which has been detected by the second sense amplifier 70 between a second pair of locations 38a and 42a. The RVCS EGM 172 may be converted to digital data by the analog-to-digital converter 124 and stored in the memory 90 by DMA controller 126 for analysis by the microprocessor 88. The RVCS EGM segment 172 includes a representation of a detected depolarization activation wave or R wave 174 which has a peak 176. The RVCS EGM 172 further has an initial portion 178 with a positive slope and a final portion 180 with a negative slope. The RVCS EGM 172 has a peak width 177 measured at a predetermined voltage 179.

FIG. 2 still further shows a representation of a detected threshold event 182, as detected by the second R wave detector 76. When the signal level of the RVCS EGM received by the second R wave detector 76 exceeds a predetermined threshold, the second R wave detector 76 provides an electrical indication such as RVCS threshold event 182 to the microprocessor 88. The detected RVCS threshold event 182 may be stored in memory 90 as the time at which the second R wave detector 76 detected a threshold event between locations 38a and 42a.

The operation of the atrial defibrillator 30 will now be described with reference to FIG. 4 and with respect to a preferred embodiment of the present invention. For purposes of this discussion, it is assumed that the atrial fibrillation detector 118 has detected an atrial fibrillation episode and that the storage capacitor within circuit 140 has been charged to a predetermined peak voltage.

Figure 3:
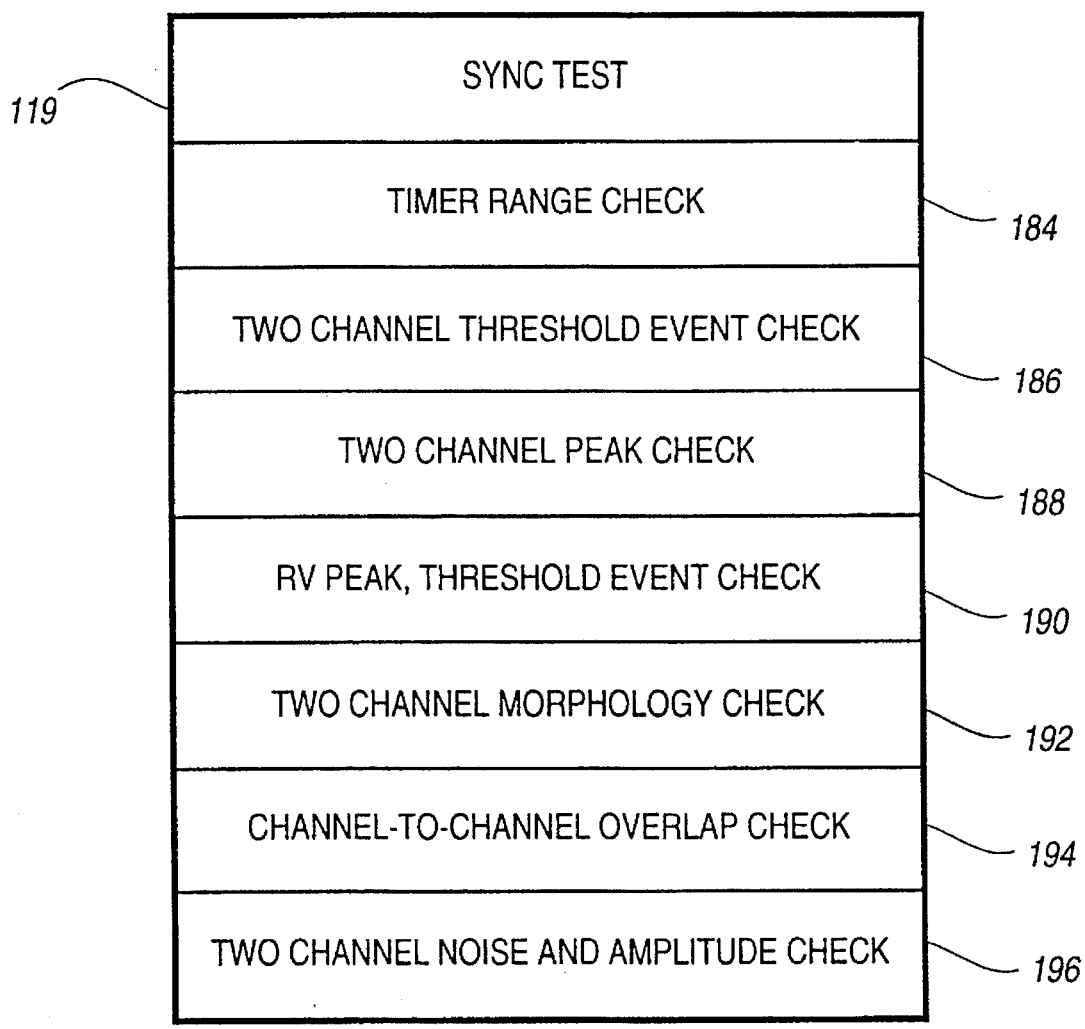
FIG. 3 is a block diagram of the synchronization test functional stage implemented by the microprocessor of FIG. 1.

FIG. 3 is a block diagram of the synchronization test functional stage 119 implemented by the microprocessor 88 of FIG. 1. In accordance with the preferred embodiment of the present invention, after the atrial fibrillation detector 118 has detected an atrial fibrillation episode and after the storage capacitor within circuit 140 has been charged to a predetermined peak voltage, the synchronization test 119 operates to synchronize the delivery of cardioverting or defibrillating electrical energy from the storage capacitor in circuit 140 with an R wave detected by the RV channel 60.

The synchronization test functional stage 119 preferably includes a number of independent tests or checks to verify the consistency of R waves detected by RV channel 60 and the RVCS channel 62. Operation of the synchronization test functional stage 119 will be discussed in further detail in conjunction with FIGS. 4 and 5.

These checks includes a timer range check 184 for verifying that the interval timed between successive R waves by the interval timer 116 is greater than a predetermined minimum and less than a predetermined maximum. The synchronization test 119 further includes a two-channel threshold event check 186 for verifying timing between R waves or threshold events detected by RV channel 60 and RVCS channel 62. The synchronization test functional stage 119 further includes a two-channel peak test 188 for verifying the time relationship between peak values of R waves detected by RV channel 60 and RVCS channel 62.

The synchronization test functional stage 119 still further includes an RV peak and threshold event check 190 for verifying the time relation between the peak value and the detected threshold event measured by the RV channel 60. The synchronization test functional stage 119 further includes a two-channel morphology check 192 for verifying the amplitudes and durations of portions of depolarization activation waves detected by the RV channel 60 and the RVCS channel 62. The synchronization test functional stage 119 still further includes a channel-to-channel overlap test 194 for verifying the time relationship of predetermined portions of the depolarization activation wave detected by the RV channel 60 and the RVCS channel 62. The synchronization test functional stage 119 further includes a two-channel noise and amplitude check 196 for verifying that the depolarization activation waves detected by the RV channel 60 and the RVCS channel 62 satisfy predetermined noise and amplitude range criteria.

The checks or tests which are included in the synchronization functional test stage 119 are preferably performed by the microprocessor 88 in response to instructions and data stored in the memory 90. The microprocessor 88 may perform one or more of the tests or checks illustrated in FIG. 3 and may perform other verification tests not illustrated there.

The operation of the atrial defibrillator 30 will now be described with reference to FIG. 4 and with respect to a preferred embodiment of the present invention. For purposes of this discussion, it is assumed that the atrial fibrillation detector 118 has detected an atrial fibrillation episode and that the storage capacitor within circuit 140 has been charged to a predetermined peak voltage.

Figure 4A:
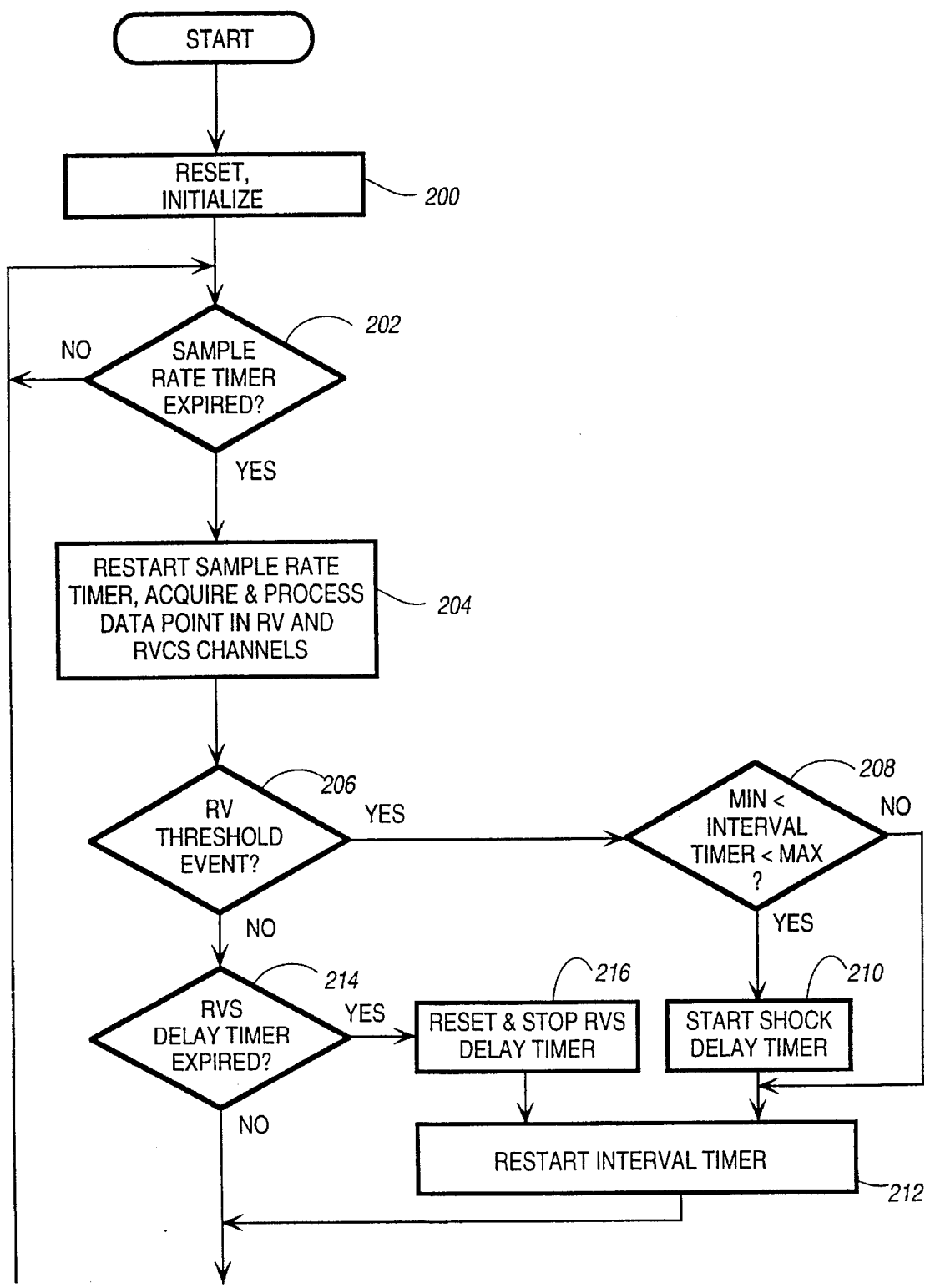
FIG. 4 is a flow diagram illustrating the manner in which the atrial defibrillator of FIG. 1 may be implemented in accordance with the present invention for reliably detecting depolarization activation waves of the heart and applying cardioverting electrical energy to the heart.
Figure 4B:
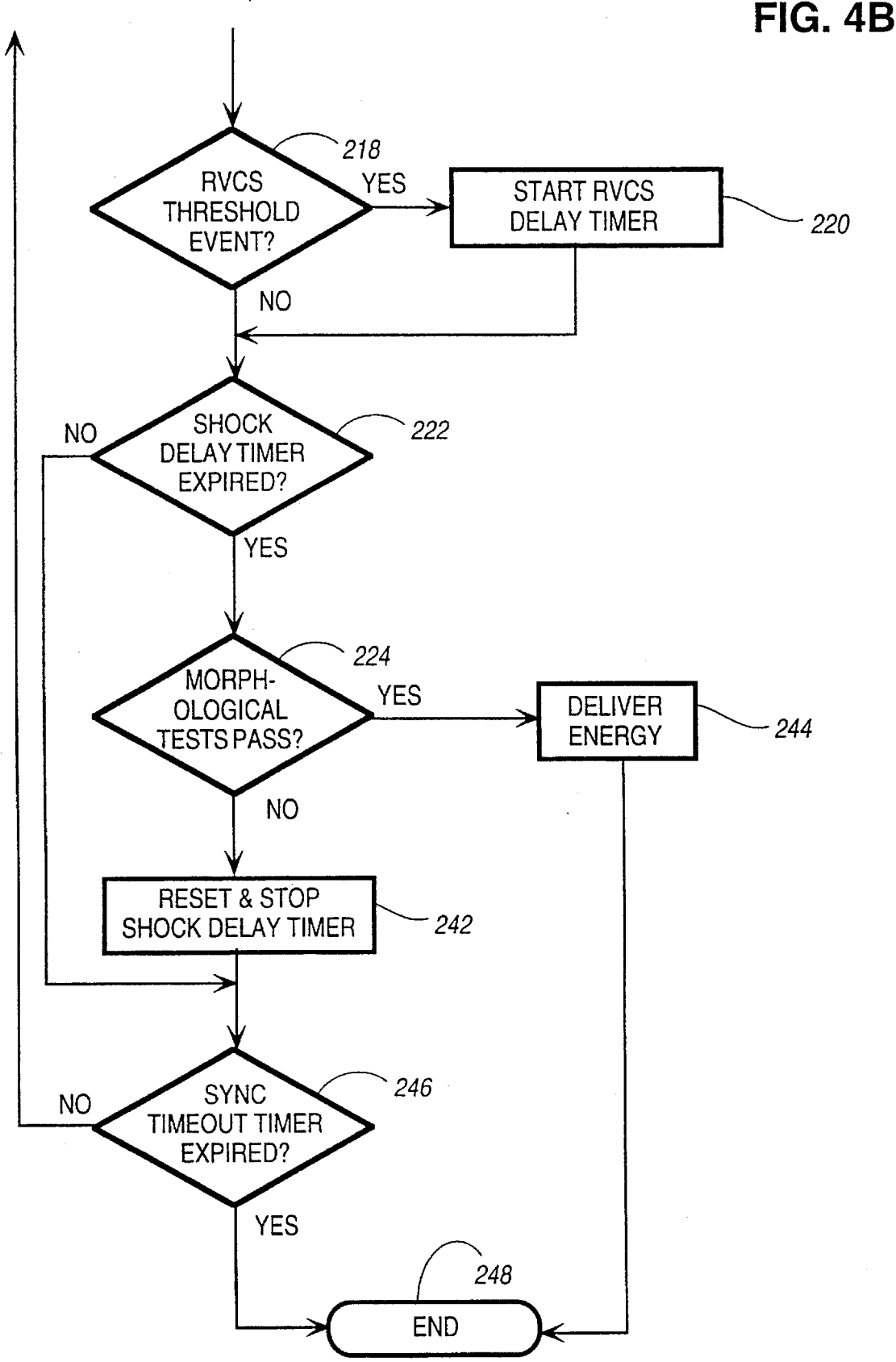

Referring now to FIG. 4, the microprocessor 88 first, in step 200, resets and initializes elements used for synchronizing delivery of cardioverting or defibrillating electrical energy to a detected R wave. The microprocessor 88 resets the sample rate timer 123 (FIG. 1), the synchronization timeout timer 125, the shock delay timer 127 and the RVCS delay timer 129. Also at step 200, the microprocessor 88 starts the sample rate timer 123 and initiates a multi-channel EGM data acquisition from the RV channel filter output 96 and the RVCS channel filter output 104. The sample rate timer 123, upon expiration, signals that a single data sample has been acquired by the DMA controller 126 from both the RV channel filter output 96 and the RVCS channel filter output 104. Upon said expiration, the microprocessor 88 may then process the digital data sample acquired from each of these two channels.

Also at step 200, the microprocessor 88 starts the interval timer 116 in response to a ventricular activation (R wave) detected by either the RV channel 60 or the RVCS channel 62. An R wave is detected if the RV EGM 160 has exceeded a predetermined threshold in RV channel 60 and the R wave detector 56 has provided an RV threshold event or initiation signal 170 to the microprocessor 88 or if the RVCS EGM 172 has exceeded a predetermined threshold in the RVCS channel 62 and the R wave detector 76 has provided an RVCS threshold event or initiation signal 182 to the microprocessor 88. After this signaling of ventricular activation, step 200 is completed and step 202 is entered.

At step 202, the sample rate timer 123 is tested. If the sample rate timer 123 has not expired, the microprocessor returns. If the sample rate timer 123 has expired, at step 204, the microprocessor resets the sample rate timer 123 and processes the most recently acquired digital data sample (stored in memory 90) from both the RV channel 60 and the RVCS channel 62. These two data samples represent a single data point on an electrogram in the RV channel 60 and the RVCS channel 62. That is, electrical activity of the heart 10 sensed by the first sense amplifier 50 and the second sense amplifier 70 is provided by the analog multiplexer 122 to the analog-to-digital converter 124 for conversion to digital data and storage by the DMA controller 126 in the memory 90. During this acquisition, the microprocessor 88 further processes this data stored in the memory 90 point by point as it is being acquired by the DMA controller 126 and as signaled by the sample rate timer 123.

The sample rate timer 123 may be reset to expire after a predetermined time interval, for example two milliseconds or four milliseconds. The sample rate timer 123 thus controls the rate at which data samples representing electrocardiograms are acquired from the RV channel 60 and the RVCS channel 62 after the atrial fibrillation detector 118 has detected an atrial fibrillation episode. While the DMA controller 126 is acquiring electrograms from the RV channel 60 and the RVCS channel 62, the microprocessor 88 may analyze previously-acquired electrocardiogram data, for example, by performing morphology tests described below in conjunction with FIG. 5.

It is desirable to apply cardioverting or defibrillating electrical energy to the atria of the heart immediately subsequent to detection of an R wave, to minimize the risk of induced ventricular fibrillation. However, R waves detected by the RV channel 60 at locations 38a and 40a (FIG. 1) tend to have widely varying amplitudes, particularly when the heart 10 is in atrial fibrillation. Therefore, there is a risk that a low amplitude R wave may not be detected by the RV channel 60, meaning the interval timer 116 may not be reset, and causing the interval timer 116 to measure a falsely long interval. To ensure that all R waves are detected and cause the interval timer 116 to be reset, the atrial defibrillator 30, in accordance with the present invention, resets the interval timer 116 in response to detection of an R wave by either the RV channel 60 or the RVCS channel 62.

Since the cardiac activity detected by the RVCS channel 62 tends to be noisy, due to atrial fibrillation and other noise, and because an R wave detected by the RVCS channel 62 tends to be spread out in time, it is preferable to apply cardioverting or defibrillating electrical energy only in response to an R wave detected by the RV channel 60. However, as can be seen from FIG. 2, an RVCS EGM 172 detected by the RVCS channel 62 may be spread out in time relative to an RV EGM 160 detected by the RV channel 60. RVCS threshold event 182 may actually be detected earlier in time than an RV threshold event 170 is detected for the same depolarization activation wave. Therefore, in accordance with the present invention, resetting of the interval timer 116 in response to an RVCS threshold event 182 is delayed by a predetermined time, such as 20 milliseconds, which is timed by the RVCS delay timer 129. Resetting of the interval timer 116 in response to an RV threshold event 170 is preferably not delayed. The RVCS delay timer 129, which establishes the delay time for resetting the interval timer 116 in response to an RVCS threshold event 182 is preferably programmable using the external controller 146. The dual reset process, including delaying the resetting of the interval timer 116 in response to a detected RVCS threshold event 182 allows application of cardioverting or defibrillating electrical energy to be accurately synchronized to an R wave detected in the RV channel 60.

To begin this dual reset process, the microprocessor 88 at step 206 first determines if an RV threshold event has occurred. An RV threshold event has occurred if the RV EGM 160 has exceeded a predetermined threshold in the RV channel 60 and the R wave detector 56 has provided an initiation signal 170 to the microprocessor 88.

If an RV threshold event has been detected, at step 208, the microprocessor 88 determines if the time interval since the last RV threshold event or the last RVCS threshold event, measured by the interval timer 116, is within a predetermined range. The range is determined by minimum and maximum time intervals which may be set from external to the implanted atrial defibrillator 30 by means of the external controller 146 and the transmitter/receiver 148. In accordance with the preferred embodiment of the present invention, the minimum time interval may be in the range of 500 milliseconds and the maximum time interval may be in the range of 2,000 milliseconds. If the time interval measured by the interval timer 116 is less than the minimum time interval or greater than the maximum time interval, the microprocessor 88 restarts the interval timer at step 212. No cardioverting or defibrillating electrical energy will be applied in response to the RV threshold event detected at step 206, and the microprocessor 88 will wait until a subsequent RV threshold event is detected before applying cardioverting or defibrillating electrical energy. If the time interval measured by the interval timer 116 is within the predetermined range of interval times, the microprocessor 88 at step 210 starts the shock delay timer 127 and at step 212 restarts the interval timer 116.

If an RV threshold event was not detected by the microprocessor 88 at step 206, at step 214 the microprocessor 88 determines if the RVCS delay timer 129 has expired. The RVCS delay timer 129 may have been started in response to a previously detected RVCS threshold event. If the RVCS delay timer has expired, at step 216, the microprocessor 88 resets and stops the RVCS delay timer and at step 212 restarts the interval timer.

At step 218, the microprocessor 88 determines if an RVCS threshold event has been detected. An RVCS threshold event is detected if the RVCS EGM 172 has exceeded a predetermined threshold in the RVCS channel 62 and the R wave detector 76 has provided an initiation signal 182 to the microprocessor 88. In response to detection of an RVCS threshold event, the microprocessor 88 starts the RVCS delay timer 129 at step 220.

At step 222, the microprocessor 88 determines if the shock delay timer 127 has expired. The shock delay timer 127 was started at step 210 in response to detection of an RV threshold event that satisfied the R-to-R interval criterion. The shock delay timer 127 ensures that cardioverting or defibrillating electrical energy will only be applied a predetermined delay time after detection of an RV threshold event which satisfies the R-to-R interval criterion. For example, the shock delay timer 127 may delay application of cardioverting or defibrillating electrical energy by 30–50 milliseconds following detection of an RV threshold event which satisfies the R-to-R interval criterion. The predetermined delay time measured by the shock delay timer 127 is preferably programmable using the external controller 146. If the microprocessor 88 determines at step 222 that the shock delay timer has expired, at step 224 the microprocessor 88 determines if the RV EGM 160 and the RVCS EGM 172 satisfy a set of predetermined morphological tests or checks, illustrated in FIG. 5.

Figure 5:
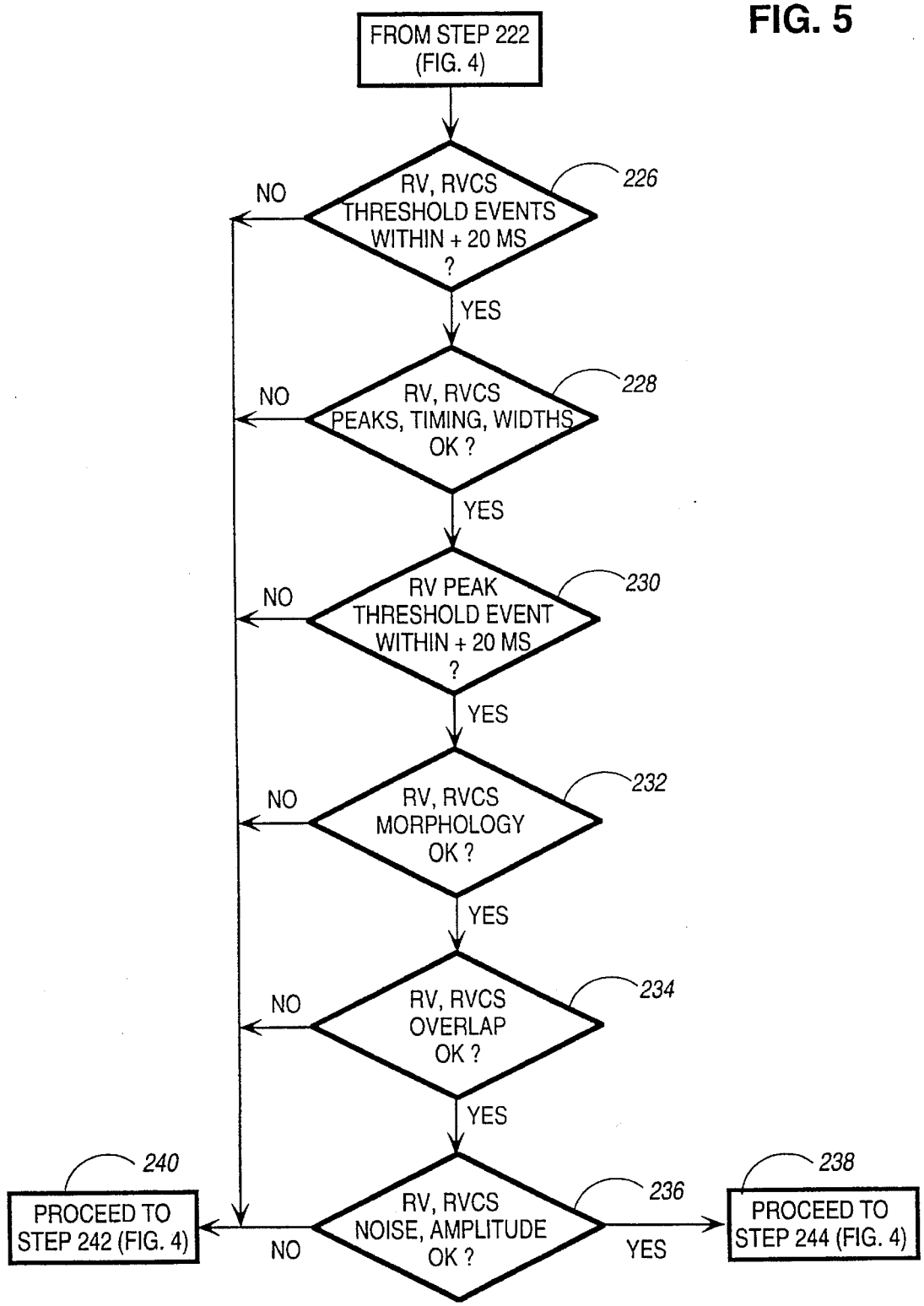
FIG. 5 is a flow diagram illustrating the manner in which the atrial defibrillator of FIG. 1 may be implemented in accordance with the present invention for performing morphological consistency analysis on detected depolarization activation waves in conjunction with the flow diagram of FIG. 4.

Referring to FIG. 5, it shows a flow diagram illustrating the manner in which the atrial defibrillator of FIG. 1 may be implemented in accordance with the present invention for performing morphological consistency analysis on detected depolarization activation waves in conjunction with the flow diagram of FIG. 4. In performing the steps illustrated in FIG. 5, the microprocessor 88 analyzes data stored in the memory 90 corresponding to electrical activity of the heart 10 detected by the first sense amplifier 50 and the second sense amplifier 70 (FIG. 1). To the degree possible, this analysis is performed on a point-by-point basis as the data is being acquired as indicated in step 204. This real-time analysis minimizes the computational time required to perform the decisions shown in FIG. 5 so that defibrillating electrical energy can be delivered as quickly as possible after the expiration of the shock delay timer 127.

To ensure that the atrial defibrillator 30 does not apply cardioverting or defibrillating electrical energy to the atria of the heart 10 in response to an erroneously detected R wave or threshold event, the atrial defibrillator in accordance with the present invention performs morphological and threshold consistency checks in addition to the R-to-R interval timing test. The morphology of a detected depolarization activation wave is the shape, duration and amplitude characteristics of the depolarization activation wave. As discussed above in relation to FIG. 1, a digital representation of a detected depolarization activation wave segment is stored in the memory 90 for analysis by the microprocessor 88. In addition, morphological analysis and consistency checks are performed in accordance with the present invention using R wave segments and threshold events detected by both the RV channel 60 and the RVCS channel 62. Before cardioversion or defibrillation can occur, the R wave segments and threshold events must meet predetermined criteria to ensure that a detected R wave is a genuine or legitimate R wave. Thus, cardioverting or defibrillating electrical energy is applied to the atria of the heart only when the atria of the heart are in need of cardioversion and when a first signal detected by the RV channel 60 satisfies a first criterion and when a second signal produced by the RVCS channel 62 satisfies a second criterion.

At step 226, the microprocessor 88 determines if threshold events detected by the RV channel 60 and the RVCS channel 62 occurred within a predetermined time with respect to each other, for example 20 milliseconds. The predetermined time may be programmable using the external controller 146. If a detected R wave is a genuine R wave, it must be detected in both the RV channel 60 and the RVCS channel 62 within a predetermined time. If the detected depolarization activation wave does not pass these criteria, the microprocessor 88 proceeds to step 242 (FIG. 4).

At step 228, the microprocessor 88 determines if the morphological peaks of the depolarization activation wave segments detected by the RV channel 60 and the RVCS channel 62 occur within a predetermined time period, such as 20 milliseconds. The predetermined time period is preferably programmable using the external controller 146. In performing this test, the microprocessor 88 determines the peak 164 of an RV EGM 160 and the peak 176 of an RVCS EGM 172 (FIG. 2). If the time relationships between the peaks 164 and 176 do not satisfy these criteria, the microprocessor 88 proceeds to step 242.

Also at step 228, the microprocessor 88 determines if the widths of the morphological peaks of the detected depolarization activation wave segments are within a predetermined peak width time range. For example, the width 165 of the RV EGM 160 (FIG. 2) must be less than a maximum width, such as 50 ms, and greater than a minimum width, such as 12 ms. Similarly, the width 177 of the RVCS EGM 172 must be less than a maximum width and greater than a minimum width. The respective maxima and minima are preferably independently definable.

At step 230, the microprocessor 88 determines if the morphological peak 164 of the R wave detected by the RV channel 60 occurs within a predetermined time, such as 20 milliseconds, of the RV threshold event 170 detected by the RV channel 60. The predetermined time interval is preferably programmable using the external controller 146. The peak 164 of the RV EGM 160 should occur within a predetermined time of the RV threshold event 170. If the R wave detected by the RV channel 60 does not satisfy these criteria, the microprocessor 88 proceeds to step 242.

At step 232, the microprocessor 88 determines if the RV EGM 160 detected by the RV channel 60 and the RVCS EGM 172 detected by the RVCS channel 62 satisfy predetermined morphology criteria. For example, the microprocessor 88 may determine if the amplitudes of the initial portion 166 and the final portion 168 of the RV EGM 160 are within a predetermined range of values. Similarly, the microprocessor 88 may determine if the amplitudes of the initial portion 178 and the final portion 180 of the RVCS EGM 172 are within a predetermined range of values. Also, for example, the microprocessor 88 may determine if the durations of the initial portion 166 and the final portion 168 of the RV EGM 160 are within a predetermined range of values, and if the durations of the initial portion 178 and the final portion 180 of the RVCS EGM 172 are within a predetermined range of values. These tests ensure that cardioverting or defibrillating electrical energy will be delivered to the atria of the heart 10 only in response to a genuine R wave, and that the detected R wave is a genuine R wave and is not contaminated with noise or other interference. If the detected RV EGM 160 and RVCS EGM 172 do not satisfy these criteria in step 232, the microprocessor 88 proceeds to step 242.

At step 234, the microprocessor 88 determines if the duration of the final portion 180 of a detected RVCS EGM 172 exceeds the duration of the final portion 168 of a detected RV EGM 160 by a predetermined time, such as four milliseconds. The predetermined time may be programmable in response to external controller 146. This test helps to ensure that detected cardiac activity has a physiological origin rather than an extraneous origin, such as noise. R waves detected by the RVCS channel 62, such as RVCS EGM 172, generally exhibit trailing R wave durations, such as final portion 180, that exceed trailing R wave durations of R waves detected by the RV channel 60, such as final portion 168. If the detected RV EGM 160 and the detected RVCS EGM 172 do not satisfy these criteria, the microprocessor 88 proceeds to step 242.

At step 236, the microprocessor 88 determines if detected signal quality is sufficient to ensure that a genuine R wave has been reliably detected. For example, the microprocessor 88, in analyzing RV EGM 160 stored in the memory 90, may determine all portions of the detected RV EGM 160, such as initial portion 166 and final portions 168, which exceed a predetermined amplitude (the amplitude threshold). If the number of such portions exceeds a predetermined number (the count threshold), then the microprocessor 88 may conclude that the detected RV EGM is noisy and is of insufficient quality. A similar test may be performed on the detected RVCS EGM 172. The amplitude threshold and the count threshold are preferably programmable, for both the RV channel 60 and the RVCS channel 62, using the external controller 146.

An additional test that may be performed at step 236 is analysis of the maximum amplitude of the detected RV EGM 160 and the detected RVCS EGM 172. For example, the microprocessor 88 may determine that the peak value 164 of the detected RV EGM 160 is within a predetermined range of values and that the peak value 176 of the detected RVCS EGM 172 is within a predetermined range of values. This ensures that, for example, the analog-to-digital converter 124 did not saturate during the R-to-R interval preceding delivery of cardioverting or defibrillating electrical energy. If the detected RV EGM 160 and the detected RVCS EGM 172 do not satisfy these criteria, the microprocessor 88 proceeds to step 242.

The precise ordering of the tests illustrated in steps 226–236 is not critical. Preferably, the detected cardiac activity must satisfy all the criteria in these steps or tests before the discharge circuit 142 applies the cardioverting or defibrillating electrical energy to the atria of the heart. However, one or more of these tests may be eliminated while remaining within the scope of the present invention. In addition, to conserve energy stored in the depletable energy source 144, it may be preferable to perform computationally simple tests first.

Referring again to FIG. 4, at step 244, if the detected ventricular activation has satisfied each of the predetermined morphology and consistency criteria (steps 226–236), and if the time interval between the last two immediately successive ventricular activations as measured by the interval timer is greater than the preselected minimum time interval and less than the preselected maximum time interval, and if the atrial fibrillation detector 118 has determined that the atria are in need of defibrillation, the charge delivery control stage 120 of the microprocessor 88 causes the discharge circuit 142 to immediately discharge the electrical energy stored in the storage capacitor of the circuit 140 for applying the cardioverting or defibrillating electrical energy to the atria 16 and 18 of the heart 10. Since the microprocessor 88 is able to process steps 202–222 very quickly after the occurrence of the last detected ventricular activation and to process steps 226–236 very quickly after the expiration of the shock delay timer 127, the discharge circuit 142 will apply the cardioverting electrical energy to the atria of the heart substantially coincident or in synchronism with the last detected ventricular activation, as determined by the shock delay timer 127. Preferably, the discharge circuit 76 will apply the cardioverting electrical energy to the atria of the heart within 30–50 milliseconds of the last detected ventricular activation.

At step 242, if the detected ventricular activity did not satisfy the predetermined morphology and consistency criteria of any of the tests of steps 226–236, the atrial defibrillator 30 will not apply cardioverting or defibrillating electrical energy to the atria of the heart in response to the shock delay timer expiration caused by the RV threshold event detected at step 206. Instead, the microprocessor 88 resets and stops the shock delay timer 127 until a subsequent RV threshold event is detected which meets the R-to-R interval criteria.

If, at step 222, the shock delay timer 127 had not expired or if, at step 224, one or more of the morphological tests did not pass and the shock delay timer was reset at step 242, the microprocessor proceeds to step 246 to determine if the synchronization timeout timer has expired. The synchronization timeout timer 125 is used by the microprocessor 88 to interrupt the shock synchronization procedure illustrated in FIGS. 4 and 5 after a predetermined time. For example, the synchronization timeout timer 125 may be reset and started at step 200 when the microprocessor 88 begins searching for a detected ventricular activation suitable for synchronizing delivery of cardioverting or defibrillating electrical energy. The synchronization timeout timer 125 may expire after, for example, one minute, indicating that no suitable synchronization condition can be determined. To prevent continued operation of the shock synchronization procedure illustrated in FIG. 4, which may deplete the depletable energy source 144, if the synchronization timeout timer 125 has expired, the synchronization procedure terminates at step 248.

If at step 246 the synchronization timeout timer 125 has not expired, the microprocessor proceeds to step 202 and awaits the next expiration of the sample rate timer 123, which signals that the DMA controller 126 has acquired another digital data sample from each of the RV and RVCS channels 60, 62. The sample rate timer 123 expires at regular intervals, for example every two milliseconds or every four milliseconds. After every expiration of the sample rate timer 123, the steps shown in FIG. 4 and FIG. 5 are potentially executed as indicated by the decision steps in these figures.

As a result of the foregoing, the atrial defibrillator of the present invention precludes the application of cardioverting or defibrillating electrical energy to the atria of the heart in the presence of a possible vulnerable condition resulting from a cardiac rate which is too high or a cardiac rate which is suspected of being highly variable. In either case, the atrial defibrillator of the present invention greatly reduces the risk of inducing ventricular fibrillation during the application of cardioverting or defibrillating electrical energy to the atria of the heart.

In addition, the atrial defibrillator of the present invention precludes application of cardioverting or defibrillating electrical energy to the atria of the heart when detected ventricular activations do not meet predefined morphological and consistency criteria. The atrial defibrillator of the present invention thus reduces the risk of falsely detecting ventricular activations and the risk of inducing ventricular fibrillation during the application of cardioverting or defibrillating electrical energy to the atria of the heart in response to such a falsely detected ventricular activation.

While a particular embodiment of the present invention has been shown and described, modifications may be made. For example, the interval timing and morphological criteria of the present invention may be utilized to advantage in an external atrial defibrillator wherein an electrode or electrodes adhered to the surface of the skin of a patient are employed along with an R wave detector for detecting ventricular activations and surface pad electrodes are utilized for applying the cardioverting electrical energy to the atria of the heart. Such surface detecting and pad electrodes are well known in the art. Additionally, the invention may be modified by deleting any. or all tests shown in FIG. 5. For example, RVCS morphology checks could be eliminated or the RV to RVCS overlap test could be eliminated. Hence, it is therefore intended in the appended claims to cover all such changes and modifications which fall within the true spirit and scope of the invention.

What is claimed is:

1. An implantable atrial defibrillator for applying cardioverting electrical energy to the atria of a human heart, said atrial defibrillator comprising:

first detecting means for sensing a depolarization activation wave at a first location of the heart and generating a first initiation signal;

second detecting means for sensing said depolarization activation wave at a second location of the heart and generating a second initiation signal; and timing means for timing the time between immediately successive depolarization activation waves of the heart, said timing means being responsive to one of said first and said second initiation signals for commencing said timing; and cardioverting means for applying said cardioverting electrical energy to the atria of the heart when the atria of the heart are in need of cardioversion and when said timing means times a time greater than a predetermined time interval.

2. An implantable atrial defibrillator as defined in claim 1 wherein said atrial defibrillator further comprises third detecting means for sensing activity of at least one of the atria of the heart and atrial fibrillation detecting means responsive to said third detecting means for determining when the atria of the heart are in need of cardioversion.

3. An implantable atrial defibrillator as defined in claim 1 wherein said cardioverting means applies said cardioverting electrical energy to the atria of the heart when the time between immediately successive depolarization activation waves is greater than a predetermined time interval.

4. An implantable atrial defibrillator as defined in claim 1 wherein said cardioverting means applies said cardioverting electrical energy to the atria of the heart when said timing means times said time between immediately successive depolarization activation waves of the heart in response to said first initiation signal.

5. An implantable atrial defibrillator as defined in claim 4 wherein said timing means commences said timing a predetermined delay time after receiving said second initiation signal.

6. An implantable atrial defibrillator as defined in claim 1 wherein said timing means comprises a timer, said timer timing the time between immediately successive depolarization activation waves of the heart, said timer being reset in response to said one of said first and said second initiation signals.

7. An implantable atrial defibrillator as defined in claim 6 wherein said timer is reset a predetermined delay time after said timer receives said second initiation signal.

8. An implantable atrial defibrillator as defined in claim 7 wherein said cardioverting means applies said cardioverting electrical energy to the atria of the heart responsive to said timer being reset by said first initiation signal.

9. An implantable atrial defibrillator as defined in claim 1 wherein said first detecting means includes first sensing means for sensing said depolarization activation wave and first output means coupled to said first sensing means for generating said first initiation signal in response to said first sensing means.

10. An implantable atrial defibrillator as defined in claim 9 wherein said second detecting means includes second sensing means for sensing said depolarization activation wave and second output means coupled to said second sensing means for generating said second initiation signal in response to said second sensing means.

11. An implantable atrial defibrillator as defined in claim 10 wherein said timing means includes delay means for delaying said commencing of said timing responsive to said second initiation signal by a predetermined delay time.

12. A method of applying cardioverting electrical energy to the atria of a human heart in need of cardioversion, the method including the steps of:

detecting a depolarization activation wave of the heart at a first location of the heart;

generating a first initiation signal responsive to detecting said depolarization activation wave at said first location of the heart;

detecting said depolarization activation wave of the heart at a second location of the heart;

generating a second initiation signal responsive to detecting said depolarization activation wave at said second location of the heart;

timing the time between successive depolarization activation waves of the heart including the step of commencing said timing in response to one of said first and said second initiation signals; and applying said cardioverting electrical energy to the atria of the heart when the atria of the heart are in need of cardioversion and when the time between successive depolarization activation waves is greater than a predetermined time interval.

13. An method as defined in claim 12 wherein the method further comprises the steps of detecting atrial activity of the heart and determining when the atria of the heart are in need of cardioversion.

14. A method as defined in claim 12 wherein said timing step is delayed by a predetermined delay time responsive to said second initiation signal.

15. A method as defined in claim 12 wherein said cardioverting electrical energy is applied to the atria of the heart when said timing commences in response to said first initiation signal.

16. A method as defined in claim 12 wherein said timing step includes evaluating an elapsed time interval measured since an immediately preceding depolarization activation wave and initiating measurement of a subsequent time interval.

* * * * *

UNITED STATES PATENT AND TRADEMARK OFFICE
CERTIFICATE OF CORRECTION

PATENT NO. : 5,464,433

DATED : November 7, 1995

INVENTOR(S) : Harley White and John M. Adams

It is certified that error appears in the above-identified patent and that said Letters Patent is hereby corrected as shown below:

| Column | Line | |
|---|---|---|
| 1 | 64 | after "Method" add --,-- |
| 1 | 65 | after "and" add --co-pending-- |
| 3 | 62 | after "DESCRIPTION" delete --:-- |

Signed and Sealed this

Twenty-sixth Day of March, 1996

Attest:

BRUCE LEHMAN

Attesting Officer

Commissioner of Patents and Trademarks